Dec. 5, 1961 W. C. SWALL Plant Pat. 2,108
PLUM TREE
Filed Nov. 21, 1960
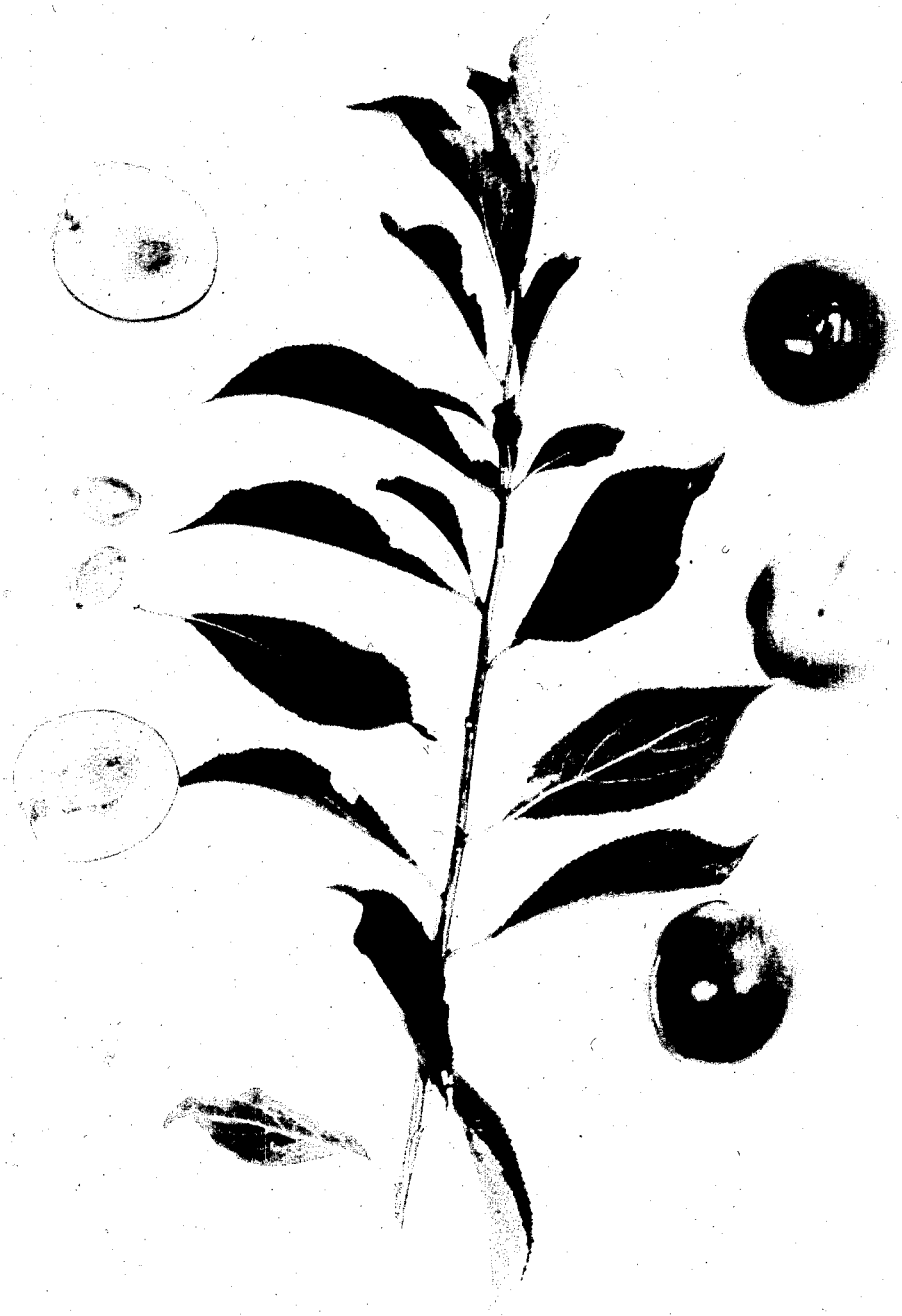
WILFRED C. SWALL
INVENTOR
HUEBNER & WORREL
ATTORNEYS
BY Richard M. Worrel United States Patent Office Plant Pat. 2,108
Patented Dec. 5, 1961

2,108
PLUM TREE

Wilfred C. Swall, Tulare, Calif.
Filed Nov. 21, 1960, Ser. No. 70,879
1 Claim. (Cl. 47—62)

The present invention relates to a new and distinct variety of plum tree.

For many years, applicant has maintained an orchard of late Santa Rosa plum trees (unpatented) on his ranch at 13339 Avenue 256 in Tulare, California. Several years ago during the regular picking season for said late Santa Rosa plums, namely between July 28 and August 15, applicant noticed that one tree in the orchard was markedly distinguished from the other trees. On said tree, all of the fruit on two limbs was green while the remainder of the fruit on the other limbs of the tree was ripe like the fruit on the other trees in the orchard. Subsequently, between August 25 and September 10 of the same growing season, applicant observed that the previously unripe fruit matured and was of good quality. Accordingly, in 1959, applicant grafted scions from said two limbs onto about two hundred seventy seedlings of the Mariana rootstock variety (unpatented). The grafts grew well and yielded about fifty lug boxes of the subject new variety of plums in 1960, all of such plums having the same late maturing and other characteristics of the fruit on said first two limbs.

The most significant features of the subject variety of plum include its maturity approximately three weeks later than the regular late Santa Rosa plum. That is, contrasted with the maturity period from between July 28 to August 15 for the late Santa Rosa plum, the subject variety matures between about August 25 and about September 10. Further, the present variety plums are smaller than the unpatented late Santa Rosa. It is recognized that the late Santa Rosa plum has a tendency to drop from the tree in the spring when the fruit is about the size of an olive; in contrast, the subject fruit does not drop from the trees in such great numbers as the late Santa Rosa. Additionally, the subject plum is somewhat lighter in color and has more yellow background than the late Santa Rosa.

The accompanying drawing shows typical specimens of the fruit and foliage of the subject plum tree taken shortly after being picked in early September. The colors are as nearly true as is reasonably possible in a color representation of this type.

The following is a detailed description of the characteristics of the subject fruit in accordance with the outline suggested by U. P. Hedrick in his book entitled "Systematic Pomology," published in 1925, and in accordance with the color terminology employed in the "Dictionary of Color" by Maerz and Paul, second edition. Where dimensions, sizes, colors, or other characteristics are given, it is to be understood that such characteristics are approximations of averages set forth as accurately as practical.

Tree: The size, figure, and shape of the subject plum tree are approximately the same as the late Santa Rosa plum tree.

*Productivity.*—Heavier than the late Santa Rosa.

*Regularity of Bearing.*—Very regular.

*Trunk.*—The diameter in relation to length and the surface characteristics of the trunk are approximately the same as the late Santa Rosa plum.

*Branches.*—Size: Similar to the late Santa Rosa. Surface character: Medium to rough on advance growth but relatively smooth on newer growth. Color: Advance growth.—Plate 14–E–4; newer growth—Bronco Old English Br.+, Plate 8–E–12. Lenticels: Typical in number and size.

*Leaves.*—Size: Similar to the late Santa Rosa. Length: Approximately average 4⅛ inches. Width: Approximate average 1⅝ inches. Shape: Similar to the late Santa Rosa. Color: Plate 23–H–8. Marginal form: Similar to late Santa Rosa. Petiole: Length—¾ of an inch; thickness —1/16 of an inch. Stem glands: Number—usually one; arranged on leaf near petiole; size—minute; type—reniform.

Flower buds: Similar to the late Santa Rosa but greater total number per tree.

Flowers:

*Dates of bloom.*—Later than the late Santa Rosa.

*Size and color.*—Similar to the late Santa Rosa.

Fruit:

*Maturity.*—Matures about three weeks later than the regular late Santa Rosa, that is, the subject variety matures between about August 25 and about September 10.

*Size.*—Smaller than the late Santa Rosa were unthinned; uniformity—very uniform; axial diameter—approximately 2 inches; transverse diameter in the suture plane—approximately 2 inches; transverse diameter at right angles to the suture plane—approximately two inches.

*Form.*—Generally uniform and spherical; symmetrical; suture—3¼ inches long, having a typical position extended from within the cavity to and terminating usually precisely at the axis, and being visible although essentially a dark line on the surface of the fruit; stem cavity—deep and nearly conical; base—rounded and symmetrically conically descending into the cavity; apex—rounded to flat; stem length—½ of an inch; stem caliper—1/16 of an inch; skin—characteristically very thin, smooth texture, some tendency to crack if allowed to stay on late in its season but not as serious as the late Santa Rosa; color—lighter than said late Santa Rosa and approximately Carbuncle+Plate 8–L–7 but tending to yellow around the cavity with Plate 10–G–6 representing such yellow, and possessing the characteristic bloom.

*Flesh.*—Color—Sunlight 10–H–4; surface of pit cavity—medium; color of pit well—approximately Sunlight 10–H–4 although darkening slightly by virtue of its attachment to the stone; juice—similar to the late Santa Rosa; flavor—not quite as sweet as the late Santa Rosa; aroma—slight but characteristically like the late Santa Rosa; texture—similar to the late Santa Rosa; fibers—typical; ripens evenly; good eating quality.

*Stone.*—Cling; elongate fibers; size—major axis length of 1 inch by minor axis length of ¾ of an inch in the suture plane by minor axis length of ⅜ of an inch at right angles to the suture plane; form—elliptic; apex—pointed; base—blunt; slightly furrowed in the base and along the edges and otherwise rough; color—Lareat, 12–C–6; no splitting tendency noticed.

*Use.*—Eating, shipping, canning.

*Keeping quality.*—Very good. The fruit can be stored under refrigeration for three or four weeks prior to shipment to eastern markets.

*Shipping quality.*—Very good.

Growth characteristics: Very hardy like the late Santa Rosa.

The new variety plum tree has been described as it exists under the ecological conditions prevailing in the central San Joaquin Valley of California. Normal variations can be expected under different environmental conditions.

Having thus described my instant plum tree, I claim:

A new and distinct variety of plum tree substantially as illustrated and described and being characterized by its late maturity approximately three weeks later than the unpatented late Santa Rosa by fruit which is smaller than the Santa Rosa and which does not drop from the trees in the spring as extensively as the late Santa Rosa, and by skin which is somewhat lighter in color and which has more yellow background than the late Santa Rosa.

No references cited.